US00PP33140P2

(12) United States Plant Patent
Clark

(10) Patent No.: US PP33,140 P2
(45) Date of Patent: Jun. 8, 2021

(54) BLACKBERRY PLANT NAMED 'A-2491T'

(50) Latin Name: ***Rubus* subgenus *Rubus* Watson**
Varietal Denomination: A-2491T

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 4 days.

(21) Appl. No.: 16/602,884

(22) Filed: Dec. 18, 2019

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 5/0887
See application file for complete search history.

(56) References Cited

U.S. PATENT DOCUMENTS

| | | | | |
|---|---|---|---|---|
| PP6,679 | P | 3/1989 | Moore | |
| PP8,510 | P | 12/1993 | Moore | |
| PP11,861 | P2 | 5/2001 | Clark et al. | |
| PP11,865 | P2 | 5/2001 | Clark et al. | |
| PP14,935 | P2 | 6/2004 | Clark | |
| PP15,788 | P2 | 6/2005 | Clark | |
| PP16,989 | P3 | 8/2006 | Clark et al. | |
| PP17,162 | P3 * | 10/2006 | Clark | A01H 6/7499 Plt./203 |
| PP17,983 | P2 | 9/2007 | Cabrera Avalos | |
| PP20,891 | P3 | 3/2010 | Clark | |
| PP22,449 | P3 | 1/2012 | Clark | |
| PP23,497 | P3 | 3/2013 | Clark et al. | |
| PP24,249 | P3 | 2/2014 | Clark | |
| PP25,864 | P3 | 9/2015 | Clark | |
| PP26,120 | P3 * | 11/2015 | Clark | A01H 6/7499 Plt./203 |
| PP26,368 | P3 | 2/2016 | Banados Ortiz et al. | |
| PP26,405 | P3 | 2/2016 | Clark et al. | |
| PP26,413 | P3 | 2/2016 | Ortiz et al. | |
| PP26,990 | P3 | 8/2016 | Clark | |
| PP27,032 | P2 | 8/2016 | Clark | |
| PP27,401 | P3 | 11/2016 | Clark et al. | |
| PP28,598 | P3 | 11/2017 | Clark | |

OTHER PUBLICATIONS

PLUTO UPOVROM Plant Variety Database Citation for 'A-2491T' as per MX PBR 2781; Dec. 4, 2018; 1 page.*
Mexican Plant Breeder's Certificate No. 2297 for variety A-2491T dated Oct. 16, 2019.
Confirmation of Filing Certificate dated Apr. 25, 2019.
MX Plant Breeders rights application as filed Oct. 30, 2018.

* cited by examiner

*Primary Examiner* — Kent L Bell
(74) *Attorney, Agent, or Firm* — Quarles & Brady LLP

(57) ABSTRACT

Description and specifications of a new and distinct cultivar of blackberry plant named 'A-2491T' that resulted from a hand-pollinated cross of 'APF-46' (non-patented, unreleased genotype) x 'Natchez' (U.S. Plant Pat. No. 20,891). This new cultivar of blackberry plant can be distinguished by its large berries with very good sub-acid fruit flavor, overall high fruit quality with excellent postharvest fruit-handling potential, early season ripening, consistent high yields, and excellent plant health.

3 Drawing Sheets

Latin name: *Rubus* subgenus *Rubus* Watson.
Varietal denomination: 'A-2491T'.

BACKGROUND

The new floricane-fruiting cultivar of blackberry with the varietal denomination of 'A-2491T' is described herein. The new cultivar originated from a hand-pollinated cross of 'APF-46' (non-patented, unreleased genotype) x 'Natchez' (U.S. Plant Pat. No. 20,891) made in 2005. The seeds resulting from this controlled hybridization were germinated in a greenhouse in the spring of 2006 and planted in a field near Clarksville, Ark. (West-Central Arkansas). The seedlings fruited in the summer of 2009 and one seedling, designated 'A-2491T', was selected for its large berries with very good sub-acid fruit flavor, overall high fruit quality with excellent postharvest fruit-handling potential, early season ripening, consistent high yields, and excellent plant health.

SUMMARY OF THE INVENTION

The new cultivar originated from a hand-pollinated cross of 'APF-46' (non-patented, unreleased genotype) x 'Natchez' (U.S. Plant Pat. No. 20,891) made in 2005 and located near Clarksville, Ark. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2006 and planted in a field near Clarksville, Ark. The seedlings fruited in the summer of 2009 on floricanes and one seedling, designated 'A-2491T', was selected for its large berries with very good sub-acid fruit flavor, overall high fruit quality with excellent postharvest fruit-handling potential, early season ripening, consistent high yields, and excellent plant health.

During 2009, the original plant selection was propagated asexually from root cuttings at the above-noted location, and a test row of 20 plants was established. Subsequently, larger test plantings have been established with asexually multiplied plants at two locations in Arkansas.

The new cultivar has been asexually multiplied annually since 2009 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants were three years old of which the pictures were taken.

Figure 1:
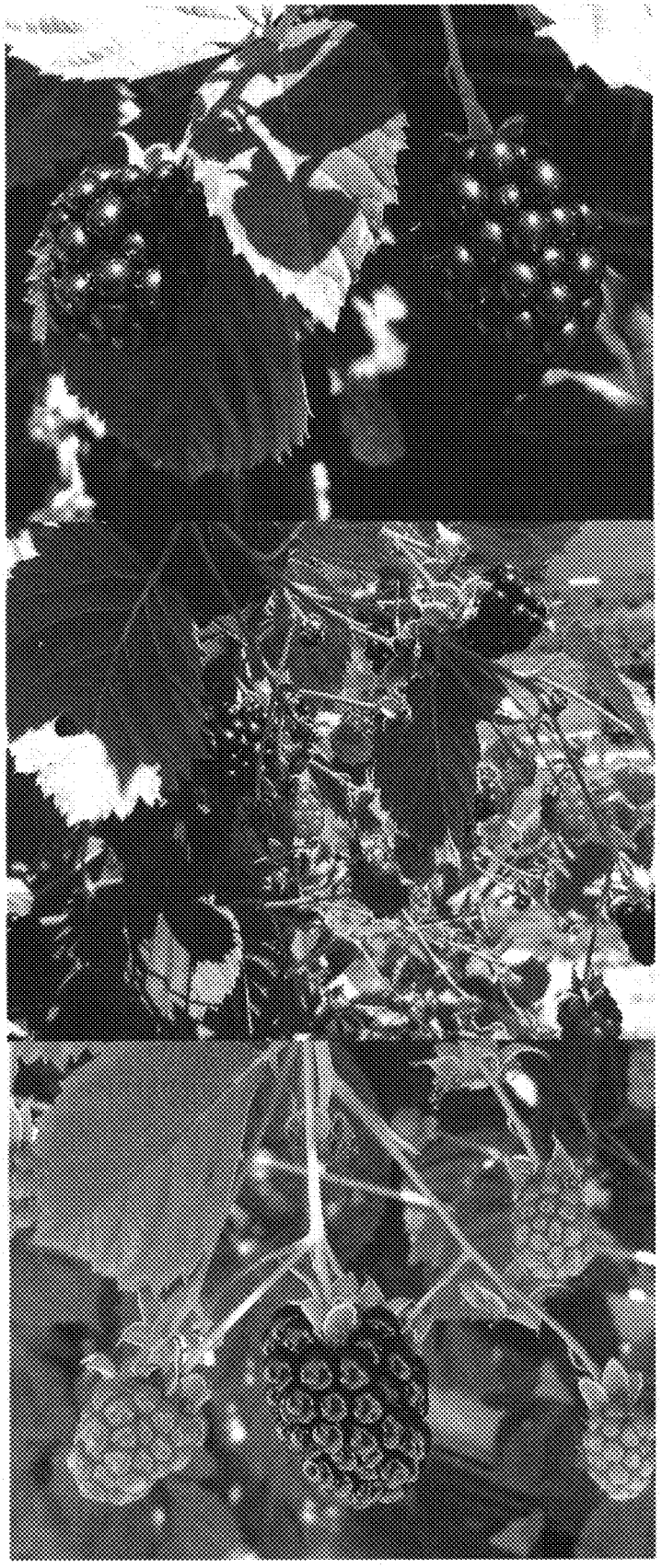

FIG. 1 includes three photographs of blackberry canes of 'A-2491T' with ripe fruit on the plant.

Figure 2:
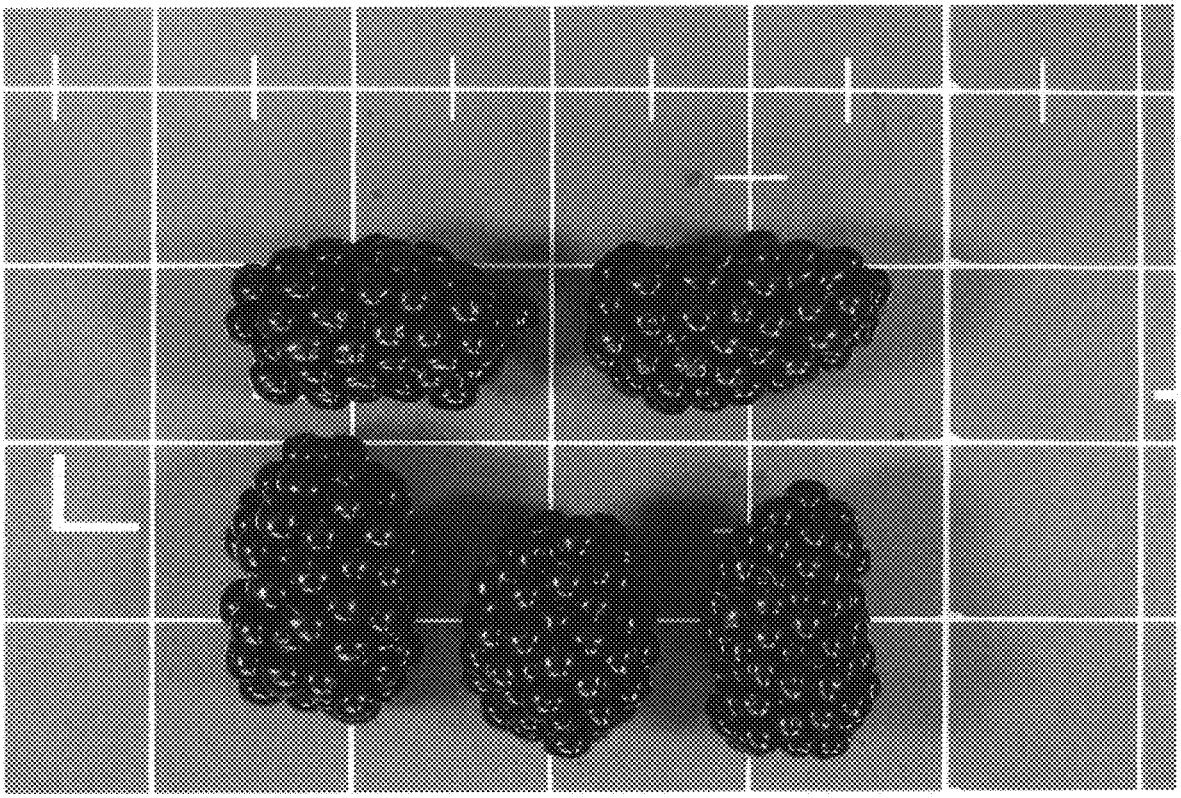

FIG. 2. is a photograph of ripe fruit of 'A-2491T'.

Figure 3:
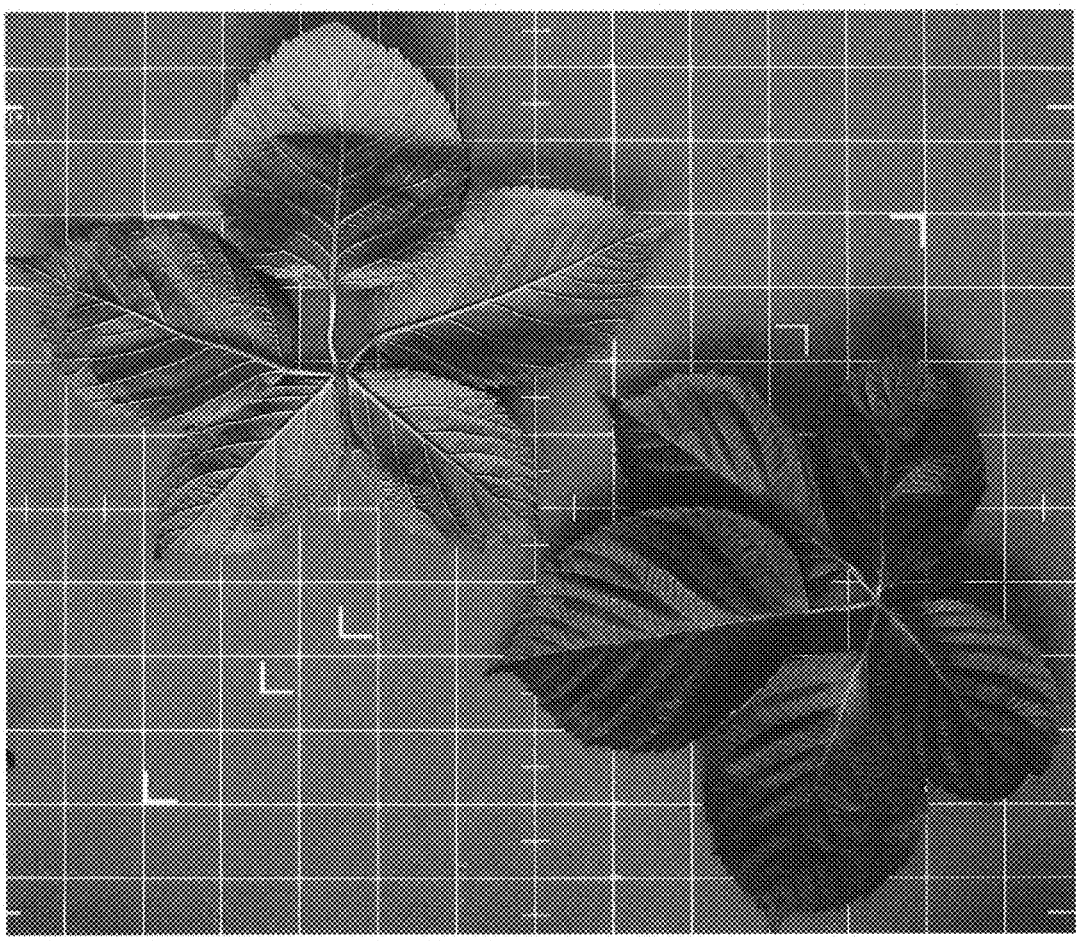

FIG. 3 is a photograph showing the abaxial and adaxial sides of a primocane leaf of 'A-2491T'.

DETAILED DESCRIPTION OF THE NEW CULTIVAR 'A-2491T'

Plants and fruit of this new cultivar differ phenotypically from its parents. The new cultivar has thornless canes, larger fruit, is higher yielding and is floricane fruiting compared to its female parent 'APF-46'. The new cultivar is lower in fruit acidity and smaller in fruit size than its male parent 'Natchez'. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit are resistant to anthracnose (*Elsinoe veneta* (Burkh.) Jenkins), and plants have shown no evidence of susceptibility to orange rust (*Gymnoconia nitens* (Schwein.) F. Kern and H. W. Thurston.). No screening has been done for resistance to double blossom/rosette (*Cercosporella rubi* (Wint.) Plakidas).

The bloom period of the new cultivar begins on average 27 April for 10% bloom and 7 May for 50% bloom and was very near that of 'APF-45' (U.S. Plant Pat. No. 22,449), 'Osage' (U.S. Plant Pat. No. 26,120) and 'Ouachita' (U.S. Plant Pat. No. 17,162).

Fruit of the new cultivar has an average first harvest date of 9 June and was very near that of 'Natchez' and 'APF-45', one day earlier than 'Osage' and four days earlier than 'Ouachita'. The average floricane fruiting period is 50 days.

Fruit yields of the new cultivar on floricanes are on average 6.1 kg (13.5 lb/plant), comparable to that for 'Natchez' in West-Central Arkansas.

The fruit is long conical shaped, glossy with a uniform black finish. The primary floricane fruit is large (ave. 9.0 g) and comparable to 'Natchez' and usually 3.0 g or larger than its similar-season comparison cultivar 'Osage', and 2.0 to 2.5 g larger than 'Ouachita'. Fruit size of the new cultivar can be reduced later in the harvest season, with average secondary and tertiary fruit sizes of 4-5.7 g berries providing for an overall seasonal fruit size average of 6.1 g. The new cultivar exhibits excellent fruit fertility with full drupelet set. Fruit firmness is a noteworthy characteristic as firmness was consistent. Red drupelet reversion was substantially less than 'Natchez'. The overall postharvest storage potential of fresh fruit of the new cultivar is greater than that of 'Natchez'.

The dry seed weight for the new cultivar averaged 4.2 mg/seed, slightly smaller than 'APF-45' (4.5 mg), 'Ouachita' (4.5 mg) and slightly larger than 'Osage' (3.8 mg).

The fresh fruit rates very well in flavor and is a noteworthy attribute of the cultivar and is comparable to or exceeding that of 'Natchez'. Consistent excellent flavor was noted at repeated observations of fruit of this cultivar over the years of evaluation. A primary fruit characteristic of 'A-2491T' is reduced acidity (0.89 g/L expressed as citric acid) compared to the more acidic 'Natchez' (1.14 g/L). The flavor is sweet and sub-acid, with desirable aromatics. The soluble solids concentration averages 9.2% on shiny black fruit, comparable to 'APF 45', 'Osage', 'Natchez', and 'Ouachita'. Fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Color Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with drip irrigation at or near Clarksville, Ark. The plants were fertilized near budbreak (late March on average) with complete or nitrogen fertilizer and had an additional nitrogen fertilizer application in early July. Primocanes were tipped at approximately 1.14 m (45 inches) and grown in a hedgerow training system. Weeds were controlled with pre- and postemergence herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size*.—Medium. Plants are grown in a hedgerow and primocanes tipped at approx., 1.14 m; plants in this system range in size from approx. 107-140 cm tall and 91-102 cm wide.

*Growth habit*.—Upright, moderate vigor, canes erect; suckers from the crown.

*Growth rate*.—Floricane first budbreak 24 February; first emergence of primocanes is 15 April and primocanes reach tipping height (107 cm) on 4 June.

Productivity:

*Floricane*.—6.1 kg/plant (13.5 lb).

Cold hardiness: Hardy to 1.4° F. (−17° C.) or lower. The low temperature of 1.4° F. was the lowest the cultivar has been exposed to and fruited successfully after this exposure.

Canes: Thornless, erect.

*Floricane* (*dormant or winter cane*).—Cane diameter: base 2.10 cm; midpoint 1.65 cm; terminal 0.74 cm.

Internode length: base 3.46 cm; midpoint 2.72 cm; terminal 4.14 cm. Floricane color: base Greyed Orange (166A) on sun-exposed portion; Green Group (143C) on shaded portion; midpoint Green Group (143A); terminus Green Group (143A).

*Primocane* (*current-season cane; late summer*).—Cane diameter: base 1.59 cm; midpoint 1.36 cm; terminal 1.09 cm. Internode length: base 3.77 cm; midpoint 3.18 cm; terminal 3.72 cm. Primocane color: base Grey Brown Group (199B) over Green Group (143A); midpoint Grey Brown Group (199B) over Green Group (143A), terminus Yellow Green Group (146B) over Grey Brown Group (199A) (sun-exposed). Anthocyanin coloration present on floricanes and primocanes with color most prevalent on sun-exposed canes. Thorn density (per 30 cm of cane length): none, plant is thornless. Disease resistance: Moderate resistance to anthracnose, and plants appear immune to orange rust. Lower susceptibility to leaf rust. No screening has been done for resistance to double blossom/rosette. Lateral branching after tipping (measured at the end of growing season): Average number of lateral branches: 3.0; distribution full length of cane.

Foliage:

*Primocane*.—Leaves: large; mature compound leaf width 21.37 cm; length 21.85 cm Leaf shape: Compound leaf shape palmate. Glossiness: Abaxial: dull, pubescence lightly present; adaxial: moderate gloss, no pubescence present. Leaflet: Width 9.35 cm; length 12.35 cm; shape lanceolate with acute apex and oblique base; margin serrated, serration teeth length 0.67 cm and width 0.46 cm; number of leaflets per compound leaf: 5; venation pinnate; young leaf abaxial vein color Yellow Green Group (146D); young leaf adaxial vein color Yellow Green Group (146C); mature leaf abaxial leaf vein color Yellow Green Group (147C); mature leaf adaxial vein color Yellow Green Group (147D); no lobing on leaflets. Color: Base abaxial Green Group (137B); adaxial Green Group (139A); midpoint abaxial Green Group (137B); adaxial Green Group (139A); terminal abaxial Green Group (137B); adaxial Green Group (139A). Petioles: Length: 3.18 cm; color: adaxial Yellow Green Group (145A) and abaxial Greyed Orange (174B); diameter 0.36 cm; texture is smooth, no pubescence. Petiolules: Length: 2.99 cm; diameter 0.20 cm; color: adaxial Yellow Green Group (145A) and abaxial Greyed Orange Group (177A); texture is light pubescence. Stipules: 2 per leaf; length: 1.47 cm; width: 0.10 cm; texture pubescence is light on abaxial surface and light on the adaxial surface. Shape: overall shape lanceolate; apex acute; base acuminate; margin: entire (smooth); Color: Green Group (141B) over Green Group (141B).

*Floricane*.—Leaves: Medium; mature compound leaf width 15.64 cm; length 9.90 cm. Leaf shape: Compound leaf shape palmate. Glossiness: Abaxial: glossy, no pubescence present; adaxial: moderate gloss, pubescence lightly present. Leaflet: Width 6.93 cm; length 8.25 cm; shape ovate with acute apex and oblique base; margin serrated, with serration teeth length 0.38 cm and width at base 0.46 cm; number of leaflets per compound leaf: 3; venation pinnate; young leaf abaxial vein color Yellow Green Group (147C); young leaf adaxial vein color Yellow Green Group (152A); mature leaf abaxial leaf vein color (147C); mature leaf adaxial vein color Yellow Green Group (147A); no lobing on leaflets. Color: Base abaxial Green Group (138A); adaxial Green Group (137A); midpoint abaxial Green Group (138A); adaxial Green Group (137A); terminal abaxial Yellow Green Group (138A); adaxial Green Group (137A). Petioles: Length 4.19 cm; color: Greyed Orange Group (177A); diameter 0.30 cm; texture waxy and smooth, very light pubescence. Petiolules: Length 1.79 cm; diameter 0.17 cm; Color: Yellow Green Group (145A) over Greyed Orange Group (177A); diameter 0.17 cm; texture is smooth and waxy with very light pubescence. Stipules: 2 per leaf; length 1.04 cm; width: 0.23 cm; texture pubescence is moderate on abaxial side and moderate on adaxial side. Shape: overall shape lanceolate; apex acute; base acuminate; margin: entire (smooth); Color: Green Group (139B) on both abaxial and adaxial surfaces.

Flowers:

*Floricane*.—Date of bloom: First bloom 27 April; 50% bloom 7 May. Reproductive organs: Stamens — erect, numerous. Pistils — numerous. Pollen — normal, fertile, and abundant. Flower: Diameter: 3.49 cm; depth: 1.28 cm; shape: overall: rotate; symmetry: actinomorphic. Petals: Number per flower: 5; length 1.77 cm; width 1.33 cm; shape: overall: saucer-shaped; apex: rounded; margin: entire (smooth); base: acuminate;

color: White Group (155D), identical color on both sides of petals. Petal Texture: Abaxial: no pubescence; adaxial; no pubescence Flowers per cluster: 13. Sepals: Number per flower: 5; length 1.02 cm; width: 0.44 cm; Shape: overall: deltoid; apex: acuminate; margin: entire (smooth); base: truncate; Texture: abaxial: moderate pubescence; adaxial: heavy pubescence; Color: abaxial: Yellow Green group (144A) with tip Red Purple Group 64-A; adaxial: Yellow Green Group (145B). Pedicel: Length: 5.19 cm; width: 1.02 cm; Color: green group (138A); texture: heavy pubescence. Peduncle: Length: 4.61 cm; width: 0.13 cm; color: Yellow-Green Group (143A). Cyme: Type: simple cyme; length: 14.4 cm.

Fruit:

*Maturity*.—Average first ripe date 9 June; average fruiting period 50 days.

*Size*.—Large, average 6.1 g for the fruiting season with primary berries average 9.0 g.

*Diameter of fruit at primary position on inflorescence*.—Equator 2.13 cm; base pole 1.83 cm; terminal pole 1.28 cm.

*Diameter of fruit at secondary positions on inflorescence*.—Equator 1.80 cm; base pole 1.49 cm; terminal pole 1.12 cm.

*Primary fruit*.—Length: 3.33 cm; Shape: long conical; Color: Black Group (202A).

*Drupelet size*.—0.48 cm.

*Drupelet number per fruit*.—84.

*Seed*.—Average length 0.38 cm; width 0.26 cm; dry weight 4.2 mg; color wet Greyed Orange Group (177B); color dry Greyed Orange Group (165D).

*Soluble solids*.—9.2%.

*Ph*.—3.12.

*Acidity*.—0.89 g/L (expressed as citric acid).

*Processed quality*.—Not evaluated for processing.

*Uses*.—Commercial fresh market cultivar with good potential for shipping, local-market production, and home garden production.

The cultivar: The most distinctive features of the cultivar are large berries with very good, sub-acid fruit flavor, overall high fruit quality with excellent postharvest fruit-handling potential, early season ripening, consistent high yields, and excellent plant health.

I claim:

1. A new and distinct cultivar of blackberry plant named 'A-2491T' substantially as illustrated and described herein.

* * * * *